United States Patent
Koike et al.

[11] Patent Number: 5,836,504
[45] Date of Patent: Nov. 17, 1998

[54] METHOD AND APPARATUS FOR SOLDERING INSPECTION OF A SURFACE MOUNTED CIRCUIT BOARD

[75] Inventors: Shiro Koike; Yasuo Morita; Yasunori Kakebayashi; Eiji Yoshida; Taro Nishijima; Yoshikazu Mori, all of Takasago, Japan

[73] Assignee: Kabushiki Kaisha Kobe Seiko Sho, Kobe, Japan

[21] Appl. No.: 776,651

[22] PCT Filed: Aug. 8, 1995

[86] PCT No.: PCT/JP95/01569

§ 371 Date: Feb. 28, 1997

§ 102(e) Date: Feb. 28, 1997

[87] PCT Pub. No.: WO96/05714

PCT Pub. Date: Feb. 22, 1996

[30] Foreign Application Priority Data

Aug. 8, 1994 [JP] Japan ................................. 6-186002
Aug. 9, 1994 [JP] Japan ................................. 6-187075

[51] Int. Cl.[6] .......................... G01B 15/06; G01B 23/04; B23K 31/12

[52] U.S. Cl. ........................... 228/103; 228/56.5; 378/58; 378/62

[58] Field of Search ................................... 228/104, 103, 228/56.5; 378/58, 62

[56] References Cited

U.S. PATENT DOCUMENTS

| | | | |
|---|---|---|---|
| 5,012,502 | 4/1991 | Battin et al. | 228/103 |
| 5,291,535 | 3/1994 | Baker et al. | 378/62 |
| 5,463,667 | 10/1995 | Ichinose et al. | 378/58 |
| 5,561,696 | 10/1996 | Adams et al. | 378/62 |
| 5,592,562 | 1/1997 | Rooks | 378/62 |

FOREIGN PATENT DOCUMENTS

| | | | |
|---|---|---|---|
| 54-143290 | 11/1979 | Japan | 378/58 |
| 61-95337 | 5/1986 | Japan . | |
| 2-247637 | 10/1990 | Japan . | |
| 3-72249 | 3/1991 | Japan | 378/58 |
| 3-265841 | 11/1991 | Japan . | |
| 4-283740 | 10/1992 | Japan . | |
| 4-330761 | 11/1992 | Japan | 228/105 |
| 5-110244 | 4/1993 | Japan . | |

*Primary Examiner*—Patrick Ryan
*Assistant Examiner*—Jeffrey T. Knapp
*Attorney, Agent, or Firm*—Oblon, Spivak, McClelland, Maier & Neustadt, P.C.

[57] ABSTRACT

It is an object of the present invention to provide a method and an apparatus for soldering inspection of a surface mounted circuit board, which can improve an inspection accuracy by obtaining a highly accurate X-rays transmission image corresponding to a real shape of the mounted surface. An apparatus and a method for soldering inspection of a surface mounted circuit board, includes an one-side transmission image reading process (23), an one-side soldering inspection process (22,7), a both-side transmission image reading process (17), a response adjustment process (15,18) for adjusting responses of the one-side transmission image and both-side transmission image so as to make their response characteristics into uniform in a referred spatial frequency range on the basis of response characteristics to a spatial frequency concerning an image radiographic system and an image processing system at said reading processes, a subtraction process (19,16,20) for subtracting the adjusted one-side transmission image from the adjusted both-side transmission image in order to obtain an other-side transmission image, and an other-side soldering inspection process (21).

20 Claims, 9 Drawing Sheets

METHOD AND APPARATUS FOR SOLDERING INSPECTION OF A SURFACE MOUNTED CIRCUIT BOARD

TECHNICAL FIELD

This invention is related to a method and an apparatus for soldering inspection of a surface mounted circuit board on which components are mounted by soldering. Especially, this invention is related to a method and an apparatus which inspect whether soldering condition is good or bad from a X-rays transmission image which is a result of radiating X-rays.

BACKGROUND ART

There is one prior method for inspecting whether soldering condition is good or bad concerning a circuit board-on which surfaces are mounted with components by soldering, which includes a radiating process for radiating X-rays towards a surface mounted circuit board, a detecting process for detecting a transmission amount of the radiated X-rays, an indicating process of indicating the transmission amount by a X-rays transmission image as a transmission amount distribution concerning different portions of the surface mounted circuit board, and an inspection process for inspecting whether soldering condition of the surface mounted circuit board is good or bad from the X-rays transmission image. It can be judged whether the soldering condition is good or bad since figure and solder amount of soldering portion can be detected from this X-rays transmission image. Thus, an information concerning X-rays transmission density is gained from such a X-rays transmission image, which corresponds to a shielding degree of X-rays which an radiated object has. The prior method applying the X-rays transmission image possesses a superior characteristic as a soldering inspection method.

However, with respect to a circuit board of which both side surfaces are mounted, it is impossible to inspect soldering conditions only from a X-rays transmission image. Because, the transmission images of the both side surfaces overlap each other.

Therefore, in order to settle this problem, one method and one apparatus for soldering inspection of a both-side surfaces mounted circuit board are proposed in Japanese Patent Laid Open 3-218409 and Japanese Patent Laid Open 5-99643, which apply X-rays transmission images.

Prior examples of a soldering inspection to the both-side surfaces mounted circuit board will be simply explained hereinafter, which are proposed in Japanese Patent Laid Open 3-218409 and Japanese Patent Laid Open 5-99643. Hereon, the both-side surfaces mounted circuit board means the circuit board of which both side surfaces should be mounted with components.

According to the method proposed in the above-mentioned Japanese Patent Laid Open 3-218409, an one-side X-rays transmission image is obtained and memorized. Hereon, the one-side X-rays transmission image means the X-rays transmission image concerning a state where one side surface of a both-side surfaces mounted circuit board is only mounted with components.

Next, a both-side X-rays transmission image is obtained. Hereon, the both-side X-rays transmission image means the X-rays transmission image concerning a state where both side surfaces of the both-side surfaces mounted circuit board are mounted with components.

And then, an other-side X-rays transmission image is extracted by subtracting the one-side X-rays transmission image from the both-side X-rays transmission image. Hereon, an other-side X-rays transmission image means the X-rays transmission image concerning a state where other side surface of a both-side surfaces mounted circuit board is only mounted with components.

Thus, the one-side X-rays transmission image and other-side X-rays transmission image are obtained respectively through the above mentioned processes. Accordingly, the one-side soldering condition and other-side soldering condition can be inspected from the one-side X-rays transmission image and other-side X-rays transmission image respectively.

According to the method proposed in the above-mentioned Japanese Patent Laid Open 5-99643, an one-side X-rays transmission image is obtained and memorized beforehand. And then, a both-side X-rays transmission image is obtained. Next, the one-side X-rays transmission image and the both-side X-rays transmission image are aligned.

And the above mentioned one-side X-rays transmission image is subtracted from the both-side X-rays transmission image at soldering portion which should be inspected. Whereby, the one-side soldering portion and other-side soldering portion which should be inspected can be inspected respectively.

As described above, according to prior methods, an other-side X-rays transmission image is extracted by subtracting the one-side X-rays transmission image from the both-side X-rays transmission image.

By the way, the number of components tends to increase and a mount density tends to be enlarged since a demand of a compact product and so on. In such a high-density surface mounted circuit board, a X-rays transmission image also becomes complicated.

Therefore, it is requested to obtain a highly accurate X-rays transmission image corresponding to a real shape of the mounted surface in order to perform a soldering inspection of a surface mounted circuit board certainly.

However, there is problem in the above mentioned prior methods. They can not obtain any enough highly accurate X-rays transmission image to inspect soldering conditions of the above-mentioned high-density surface mounted circuit board since an other-side X-rays transmission image is extracted by just simple subtracting the one-side X-rays transmission image from the both-side X-rays transmission image.

In view of the foregoing problems with the prior art techniques, the present invention has been made. It is an object of the present invention to provide a method and an apparatus for soldering inspection of a surface mounted circuit board, which can perform a soldering inspection of a surface mounted circuit board and improve an inspection accuracy to obtain a highly accurate X-rays transmission image corresponding to a real shape of the mounted surface.

It is another object of the present invention to provide an image reader suitable to set into the apparatus for soldering inspection of a surface mounted circuit board.

The inventors paid attention to a spatial frequency while considering to obtain a highly accurate X-rays transmission image.

A response of a X-ray image intensifier to a spatial frequency is shown in FIG. 9. The X-ray image intensifier is one kind of the X-rays detectors. A response of a X-rays detector to a spatial frequency varies with a variation of a spatial frequency as understood from the FIG. 9. In other words, the response to the spatial frequency is not constant. This means X-rays transmission amounts concerning two states of a both-side surface mounted circuit board are detected with variant response. The one state is the state where one side surface of the both-side surfaces mounted circuit board has been only mounted with components. Hereon, the other state is the state where both side surfaces of the both-side surfaces mounted circuit board have been mounted with components. Because the both-side surfaces mounted circuit board in the above one state has a different spatial frequency from the both-side surfaces mounted circuit board in the other state. For this reason, any enough highly accurate other-side X-rays transmission image of the above-mentioned high-density surface mounted circuit board to be inspected soldering conditions can not be obtained under an influence due to a response characteristic of a X-ray detector.

In fact, any enough highly accurate other-side X-rays transmission image can not be obtained by prior soldering inspection method wherein an other-side X-rays transmission image is extracted by just simple subtracting an one-side X-rays transmission image from a both-side X-rays transmission image.

Especially, gain characteristic of a X-rays detector falls down in a high spatial frequency range due to communication characteristic of an image processing apparatus, so that a response of the X-rays detector becomes worse. In other words, a relation between a density information in a high spatial frequency range and a X-rays shield degree of a radiated object differs with a relation between a density information in a low spatial frequency range and a X-rays shield degree of a radiated object. It is made difficult by the above difference to obtain the X-rays transmission images corresponding to real figures of the mounted surfaces.

DISCLOSURE OF THE INVENTION

Thereat, in order to achieve the above-mentioned object, the present invention inspects soldering conditions by such a method as follows applying a soldering inspection apparatus comprising an one-side transmission image reader, an one-side soldering inspector, a both-side transmission image reader, at least one response adjustor, a subtracter and an other-side soldering inspector.

The present method for inspecting soldering conditions of a surface mounted circuit board, which the present invention applies in order to achieve the above-mentioned object, includes an one-side transmission image reading process for obtaining an one-side transmission image to radiate X-rays to a circuit board of which only one side surface is mounted with components, an one-side soldering inspection process for inspecting soldering conditions using the one-side transmission image, a both-side transmission image reading process for obtaining a both-side transmission image to radiate X-rays to the circuit board of which both side surfaces are mounted with components, a response adjustment process for adjusting responses of the one-side transmission image and both-side transmission image so as to make their response characteristics into uniform in a referred spatial frequency range on the basis of response characteristics to a spatial frequency concerning an image radiographic system and an image processing system at the reading processes, a subtraction process for subtracting the one-side transmission image of which response adjusted from the both-side transmission, image of which response adjusted in order to obtain an other-side transmission image, and an other-side soldering inspection process for inspecting soldering conditions using the other-side transmission image.

The response adjustment process may be performed by such as a process for making gain characteristics of the one-side transmission image and both-side transmission image into uniform in the referred spatial frequency range. According to the soldering inspection method of this above-mentioned invention, the one-side transmission image and both-side transmission image having different spatial frequencies respectively are adjusted so as to make their response characteristics into uniform in the referred spatial frequency range by the above-mentioned response adjustment.

Therefore, an influence from characteristic of a response which is not constant through all the spatial frequencies in the X-ray detector (for example, gain characteristic falls down in the high spatial frequency range) can be eliminated. A precise other-side transmission image can be obtained by means of subtracting the adjusted one-side transmission image from the adjusted both-side transmission image. Consequently, an accuracy of a soldering inspection is improved.

In addition, a highly accurate inspection can be performed provided that the adjusted one-side transmission image is applied at the one-side soldering inspection process.

Further, the foregoing subtraction process for subtracting the one-side transmission image from the both-side transmission image includes an alignment process as follows.

At first, information concerning standard marks are read from the one-side transmission image and the both-side transmission image respectively. Next, gap amounts between information concerning reference points on the circuit board which have given in advance and the above information concerning the standard marks are calculated respectively. And then both one-side transmission image and the both-side transmission image are aligned with an amendment for amending a slight gap between the foregoing transmission images by using the above gap amounts.

At the above mentioned alignment process, gap amount between the one-side transmission image and the both-side transmission image is under one picture element pitch. For this reason, a more accurate other-side transmission image can be obtained in comparison with a prior other-side transmission image which is obtained by means of only coinciding information concerning the standard marks which have been respectively read from both images.

Moreover, it is preferable for the one-side transmission image to be transferred after compression and coding when the one-side transmission image is transferred toward necessary processes for obtaining the other-side transmission image. Whereby a transferring speed of the one-side transmission image is improved.

Further, it is preferable that such as processes for decoding, expanding and memorizing the above compressed and coded one-side transmission image are provided. Whereby the one-side transmission image can be taken out at any times while synchronizing the both-side transmission image reading process. So that, the soldering inspections about one and other side surfaces of the circuit board can be carried out at the same time. In addition, while inspection about one circuit board is performed, an one-side transmission image of a next one circuit board can be ready. It becomes possible to carry out soldering inspection with synchronizing process for manufacturing surface mounted circuit boards.

In addition, the image reader which is suitable to be provided in apparatus for performing the above mentioned soldering inspection method of the present invention, comprises a recording means for recording a radiation transmission image of a flat circuit board onto a recording plate which consists of a radiate-out phosphor material, wherein the radiation transmission image is obtained by means of radiating a radiation perpendicularly from a radiation source positioned above the circuit board towards the recording plate below the circuit board, a reading means for reading the foregoing recorded image on the recording plate, wherein a reading operation is performed by catching a radiate-out luminous light which is irradiated out from the recording plate by means of irradiating an excitation light onto the recording plate, an erasing means for erasing the foregoing recorded image on the recording plate, wherein an erasing operation is performed by exposing the recording plate to light, a circulation conveyance means for conveying the recording plate circularly within a first horizontal plane, wherein the recording plate is conveyed circularly in order of the recording means, the reading means, the erasing means and the recording means again, and a circuit board conveyance means for conveying the circuit board within a second horizontal plane which is located upward in parallel with the first horizontal plane.

In the above mentioned image reader, a distance between the circulation conveyance means and the circuit board conveyance means can be set into narrow since the recording plate and the circuit board are conveyed within the horizontal planes which are in parallel with each other. As a result of that, a whole size of the image reader becomes compact. Moreover, it is rare for an operator to be bathed in a radiation since the radiation is radiated downward (toward a floor) in the image recording section.

It is preferable for the recording plate to be conveyed within the first horizontal plane circularly with sucked on the circulation conveyance means by a vacuum suction device. Whereby, a removal and a installation of the recording plate onto the circulation conveyance means can be done extremely simply. And also, a seting the recording plate at a desired position in the circulation conveyance-means can be done easily.

It is preferable for the recording means to have an elevator for adjusting a distance between the circuit board and the recording plate in the image recording section. Whereby, an image reading operation can be carried out whether object size is small or large. And also, a focus can be easily adjusted.

It is preferable for the reading means to have a plurality of scanning devices along the conveying direction. The scanning devices irradiate excitation lights on only one recording plate, Whereby, different portions of the foregoing recording plate can be scanned at the same time and the different portions of only one image can be recorded at the same time. Accordingly, a scanning time becomes short with inversely proportion to the number of scanning devices. Also, there is no problem of requiring a lot of time in scanning.

Furthermore, it is preferable for the plurality of scanning devices to share light beams from a common light source with each other. Whereby, an economical profitability improves.

Also, it is preferable for the plurality of scanning devices to irradiate light beams of which irradiation intensities are uniform. Whereby, a calibration of output ranges between the plurality of scanning devices becomes unnecessary.

BEST MODE FOR CARRYING OUT THE INVENTION

One embodiment which materializes the present invention will be explained referring attached figures as follows. They will be offered in understanding of the present invention. In addition, a technical scope of the present invention is not limited by only the following embodiment. The following embodiment is just one of examples which materialize the present invention.

Figure 1:
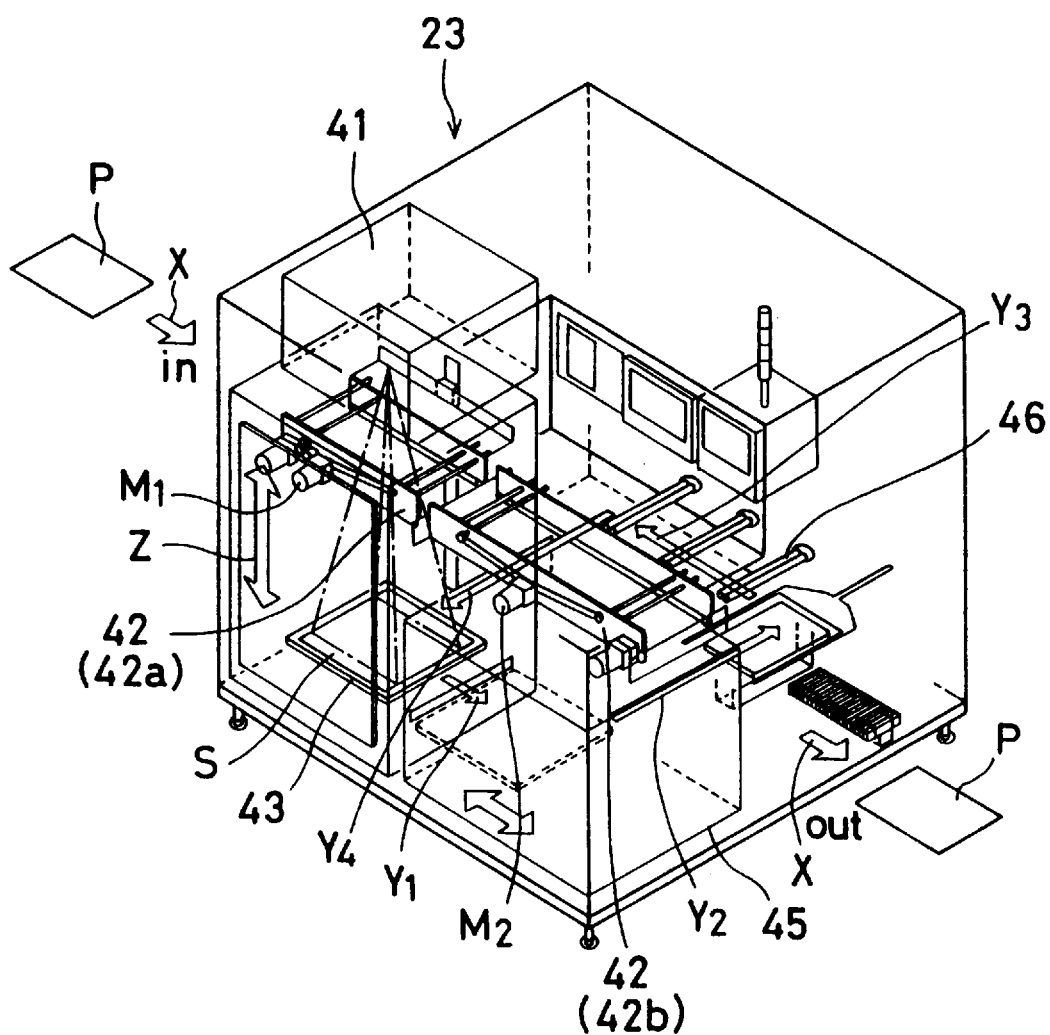
FIG. 1 depicts a perspective view of an image reader as components in it can be seen, which is provided in apparatus for executing a method for soldering inspection of a surface mounted circuit board concerning one embodiment of the present invention.

First, image reader 23 for reading a radiation transmission image applying a radiation such as a X-rays is explained based on the FIG. 1, which is provided for the apparatus to carry a soldering inspection method of a surface mounted circuit board concerning this invention.

The image reader 23 shown in FIG. 1 comprises structurally main elements as follows.

A X-rays generator 41.

A circulation conveyor, which is not shown in FIG. 1, for conveying a radiate out phosphor sheet loaded on a substrate 43 circularly within a first horizontal plane, wherein the radiate out phosphor sheet is conveyed circularly in order of arrows Y1, Y2, Y3, and Y4.

A circuit board conveyor 42 for conveying a printed circuit board P within a second horizontal plane pointed out by an arrow X, which is located upward in parallel with the first horizontal plane and which has been divided into an initial half 42a in an image recording section and a last half 42b in other section.

An erasing means 48 having a fluorescent lamp in order to erase an information of a recorded image on the radiate-out phosphor sheet conveyed into by the circulation conveyor.

In addition, the circuit board conveyor 42 can lift up and down the circuit board in the direction of arrow Z by motors M1 and M2 provided in the initial and last halves 42a, 42b respectively. Whereby, a focus can be easily adjusted in accordance with a size of the circuit board.

The circuit board is conveyed under the X-rays generator 41 as shown in FIG. 1 by the initial half 42a of the circuit board conveyor 42. And the X-rays generator 41 radiates X-rays downward. The X-rays transmitted from the circuit board is further radiated toward the radiate-out phosphor sheet S positioned under the circuit board. An image corresponding to a figure of the whole of the circuit board and soldering portions on its mounted surface is recorded on the radiate-out phosphor sheet S.

The radiate-out phosphor sheet S recording the image is conveyed into an image reader section 45 as shown by arrow Y1. Details of the image reader section 45 is shown in FIG. 2.

Figure 2:
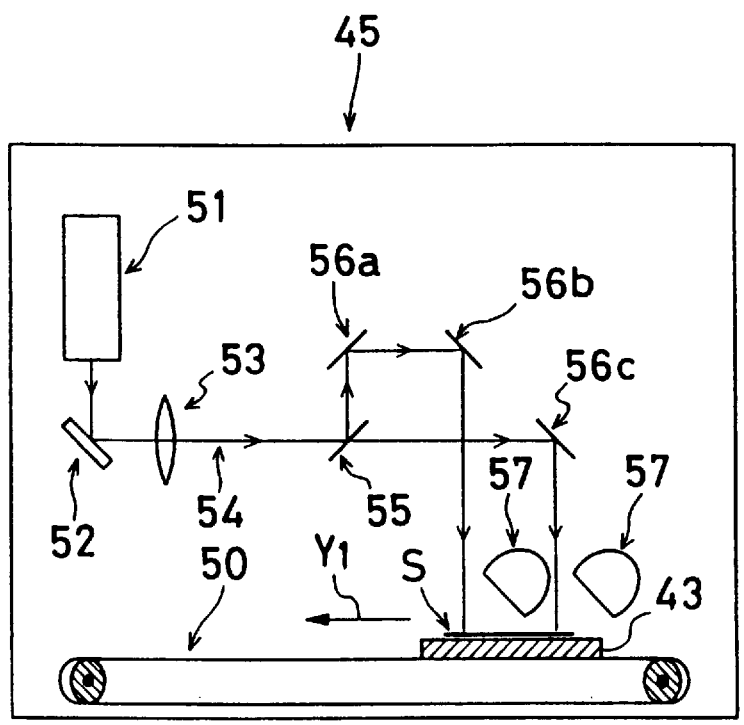
FIG. 2 is the figure for explaining a conception of scanning devices in the above image reader.

In the image reader section 45, a laser beam shown by an arrow from a laser beam oscillator 51 is deflected at a galvanometer 52 within a plane 54 crossing perpendicularly with the paper on which FIG. 2 is drawn. An aberration of the laser beam is canceled through a fθ - lens 53. And then the laser beam comes up at a half reflection mirror 55.

Hereon, the fθ - lens 53 is a lens wherein an image height image height is proportional to an incident angle (a scanning angle) θ so as to make a scanning velocity on a screen into uniform. And also the fθ - lens 53 is designed so as to close to a function of Y=fθ of which f is a focal distance.

The half reflection mirror 55 is designed so as to make a transmission probability into 50%.

A quantity of light concerning laser beam which is reflected at the half reflection mirror 55 and comes up to a first perfect reflection mirror 56a is the same quantity of light concerning laser beam which goes through the half reflection mirror 55 and comes up to a third perfect reflection mirror 56c. The laser beam reflected by the first perfect reflection mirror 56a is reflected by second perfect reflection mirror 56b toward the radiate-out phosphor sheet S loaded on the substrate 43. And, the laser beam going through the half reflection mirror 55 is reflected by third perfect reflection mirror 56c toward the radiate-out phosphor sheet S loaded on the substrate 43. Thus, the laser beam is irradiated toward the radiate-out phosphor sheet S.

The laser beam from the second perfect reflection mirror 56b is irradiated toward on a lower stream side of the radiate-out phosphor sheet S with respect to a conveyance direction Y1. The laser beam from the third perfect reflection mirror 56c is irradiated toward on a upper stream side of the radiate-out phosphor sheet S with respect to the conveyance direction Y1. Both the laser beams are irradiated on the radiate-out phosphor sheet S at the same time. This implies the same effect as two scanners are arranged in the conveyance direction.

Further, the two scanners share a laser beam from one common light source. The two scanners bring an effect of reducing a scanning time into half in comparison with only one scanner scanning the radiate-out phosphor sheet S. Hereon, the scanning time corresponds to a time for reading the image.

Moreover, an adjustment concerning the quantities of light is not necessary since quantities of light concerning both laser beams are equal to each other.

Figure 3:
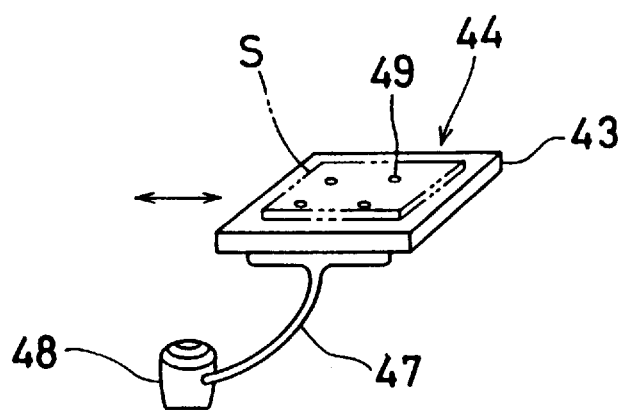
FIG. 3 depicts a perspective view of a vacuum suction device applied to the conveyance means for conveying the recording plate or the circuit board in FIG. 1.

The substrate 43 loaded with the radiate-out phosphor sheet S has a vacuum suction device on its top surface in order to set and keep the radiate-out phosphor sheet S on an appropriate position on its top surface certainly and also detach it from its top surface easily. Details of the vacuum suction device is shown in the FIG. 3. An inside of substrate 43 is hollow. A plurality of suction bores 49 formed on the top surface of the substrate 43 is communicable with an inside of a flexible tube 47 through the inside space of substrate 43. The flexible tube 47 is coupled with a vacuum source 48. Therefore, the radiate-out phosphor sheet S shown by a two dash line is set and kept to an appropriate position on the top surface of the substrate 43 certainly by means of setting the vacuum source 48 in operation after loading the substrate 43 with the radiate-out phosphor sheet S.

And also, the radiate-out phosphor sheet S is allowed to detach from the substrate 43 by means of stopping the operation of the vacuum source 48.

Visible fluorescent lights are irradiated from a territory which is made into an excitation state on the radiate-out phosphor sheet S by 2 number of laser beams irradiated toward the radiate-out phosphor sheet S.

A quantities of fluorescent light from referential positions are detected by 2 number of light detectors 57 as divided data of time. The referential position is established by a deflection (scan) angle at the galvanometer 52 and a conveyance quantity by a belt 50 within the image reading section 45.

Two-dimensional images recorded on the radiate-out phosphor sheet S can be detected as divided data of time, which corresponds to transmission quantity distribution of the X-rays concerning the circuit board and the soldering portion of it. The radiate-out phosphor sheet S on which the image has been read is conveyed in the direction of arrow Y2 by the conveyor which is not illustrated. And the radiate-out phosphor sheet S is exposed to a light of a fluorescent lump in the erasing means in order to erase an information of the recorded image on the radiate-out phosphor sheet.

The radiate-out phosphor sheet S on which the information of the recorded image is erased is further conveyed within the horizontal plane as shown by the arrows Y3 and Y4 in FIG. 1. At last, it returns under the X-rays generator 41 in the image recording section again. Thus, the radiate-out phosphor sheet S is conveyed circularly in the image reader 23. And, by repeating the above-mentioned processes, the radiate-out phosphor sheet S can be used repeatedly without being discharged.

In the above-mentioned embodiment, the light beam scanners are applied to the reader section for reading the image on the radiate-out phosphor sheet S.

Photoreceptor may be applied instead of the radiate-out phosphor sheet S. In this case, two number of light beams having quantities of light in accordance with image data respectively are irradiated toward the photoreceptor. Namely, it is possible to apply as an image former (an image writer).

By applying the above-mentioned image reader, following effects can be obtained. A distance between the circulation conveyer and the circuit board conveyer can be set into narrow since the radiate-out phosphor sheet S as the recording plate and the circuit board are conveyed within the horizontal planes which are in parallel with each other. As a result of that, a whole size of the image reader becomes compact. Moreover, there is little danger of a radiation leakage since the radiation is radiated toward a floor in the image recording section.

A image reading operation can be carried out whether object size is small or large since the circuit board can be lifted up and down in the image recording section in order to adjust the distance between the circuit board and the recording plate. And also, a focus can be easily and certainly adjusted.

In case that the radiate-out phosphor sheet S as the recording plate can be conveyed with sucked on the circulation conveyer by the vacuum suction device, a removal and a installation of the radiate-out phosphor sheet S onto the circulation conveyer can be done extremely simply. And also, there is few probability of the radiate-out phosphor sheet S moving slightly from the desired position. A scanning time reduces in inverse proportion to the number of the scanners since the plurality of scanners perform at the same time for only one scanned object. The number of light sources are reduced by a construction comprising the plurality of scanners which can be share a light beam from a common light source. Accordingly, the economical image reader can be obtained. And, it can become unnecessary to calibrate an output range of each scanner provided that all irradiation intensities of light beams from the plurality of scanners are same. Also, device for calibrating an output range of each scanner can become unnecessary. Therefore, scanners can be simplified.

Secondly, a soldering inspection method of a surface mounted circuit board concerning the present invention will be explained.

Figure 4:
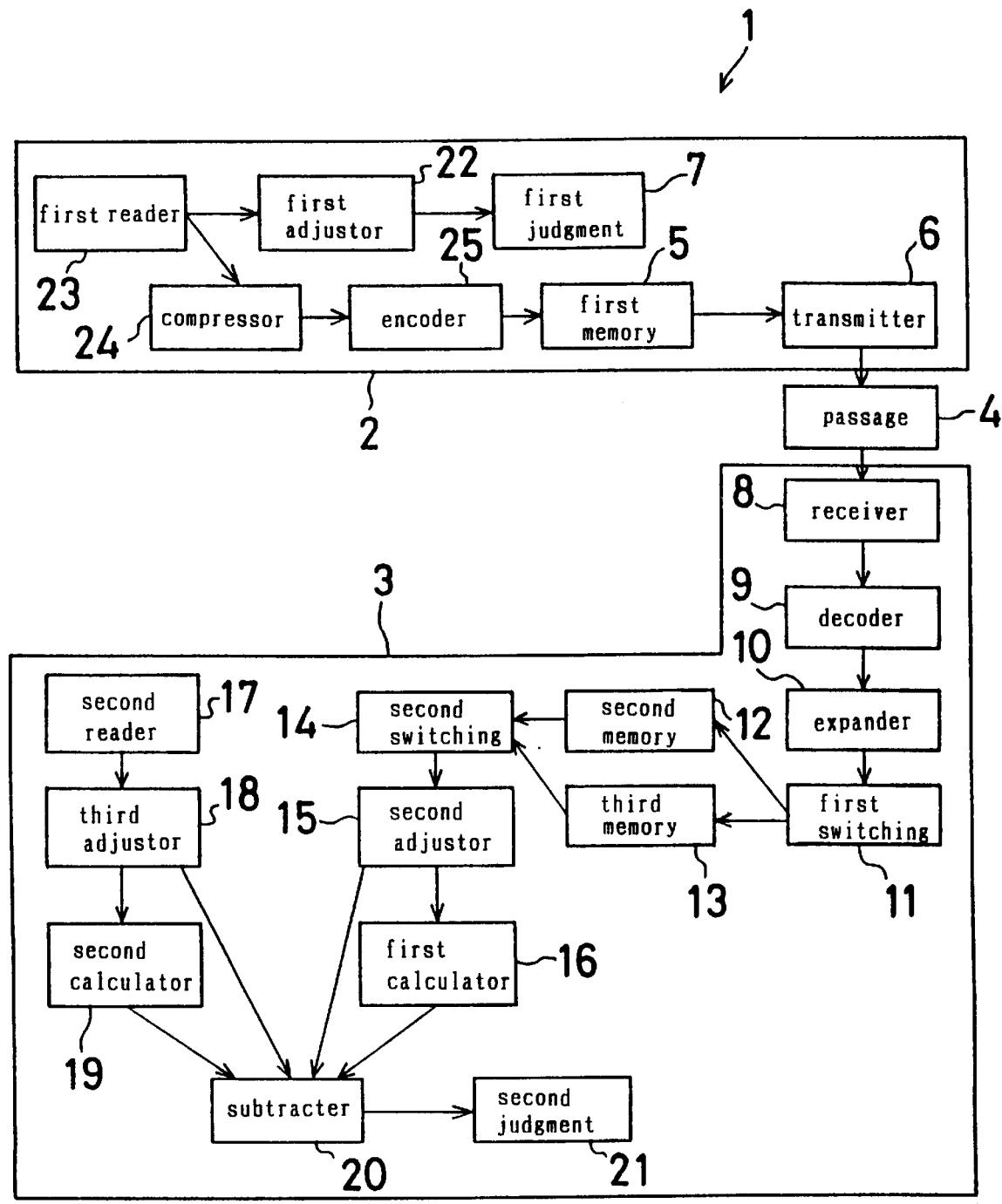
FIG. 4 depicts the block diagram which shows construction of the soldering inspection method concerning one embodiment of the present invention.

A soldering inspection apparatus 1 shown in FIG. 4 concerning one of embodiments is installed in a soldering inspection line which constitutes one part of a line for mounting components on a surface of a circuit board so as to be able to carry a soldering inspection successively after mounting components on the surface of the circuit board.

In case an inspected object is the circuit board which should be mounted with components on both side surfaces of it, the soldering inspection apparatus 1 comprises following means.

a first inspection section 2 for inspecting an one-side surface.

a second inspection section 3 for inspecting an other-side surface.

a transmission passage 4 connected to both first and second inspection sections for transferring an image data from the first inspection section 2 to the second inspection section 3.

The first inspection section 2 is stationed on a line for mounting components on the one-side surface of the circuit board and the second inspection section 3 is stationed on a line for mounting components on the other-side surface.

In case an inspected object is the circuit board which should be mounted with components on only its one side surface, the soldering inspection apparatus 1 inspects the inspected object at the first inspection section 2 only.

The first inspection section 2 for the one side surface includes a first image reader 23 for reading a X-rays transmission image, a first response adjustor 22, a first judgment device 7 for judging a defect of a mounted state, an image compressor 24, an image encoder 25, a first memory 5 and an image transmitter 6.

The second inspection section 3 for an other side surface includes an image receiver 8, an image decoder 9, an image expander 10, first and second switching devices 11 and 14, second and third memories 12 and 13, a second image reader 17 for reading a X-rays transmission image, second and third response adjustors 15 and 18, a subtracter 20, first and second standard mark calculators 16 and 19 and a second judgment device for judging a defect of a mounted state 21.

The first and second image readers 23 and 17 can judge figures of soldering portions and amounts of soldering by means of detecting a distribution concerning amounts of X-rays transmission at soldering portions of an inspected object from a X-rays transmission image as shown in FIG. 1. Whereby, we can inspect whether soldering conditions are good or bad.

A soldering inspection method for inspecting soldering conditions of a surface mounted circuit board concerning the present invention is performed by the above mentioned soldering inspection apparatus as follows..

In a X-rays transmission image obtained by the above X-rays transmission image reader 23, a gain characteristic in a high range spatial frequency falls down under an influence of a response characteristic. Accordingly, there is a problem wherein the X-rays transmission images corresponding to real figures of mounted surfaces are not obtained precisely. Therefore, gain characteristics of the transmission images are made into uniform in a referred spatial frequency range by means of adjusting responses of the transmission images on the basis of their response characteristics by the response adjustor 22. The above mentioned soldering inspection process of inspecting soldering condition from the distribution concerning amount of X-rays transmission is performed by the first judgment device 7 with applying the response adjusted transmission image.

Thus, the circuit board mounted with components on its one side surface undergoes a soldering inspection by devices such as the image reader 23, the response adjustor 22 and the first judgment device 7.

In case of the circuit board to be mounted on its one side surface only, the soldering inspection has been finished by this time. In case of the circuit board to be mounted on its both side surfaces, while the above mentioned soldering inspection for the one side surface, the one-side transmission image obtained by the first image reader 23 is compressed and coded by the image compressor 24 and the image encoder 25, and further is memorized into the first memory 5. And then, the memorized image is transferred from the first inspection section 2 to the second inspection section 3 through the transmission passage 4.

In the second inspection section 3, the transferred image is received, decoded and expanded by the image receiver 8, the image decoder 9 and the image expander 10. Whereby, the one-side transmission image is regenerate. The one-side transmission image is memorized into the second or third memory 12 or 13 properly selected by the first switching device 11.

Accordingly, transferring time of transferring the one-side transmission image is shortened since the transferred image is compressed and coded. The one-side transmission image can be transferred to the second inspection section 3 during executing processes for mounting components on an other side surface of the circuit board. Therefore, the processes for mounting components on surfaces of the circuit board and the processes of soldering inspection can be performed successively as one line.

The plurality of memories such as second and third memories store the one-side transmission image transferred from the first inspection section 2 in order of transferring, and further enable the one-side transmission images to be taken out and treated in accordance with a flow of the processes for mounting components on surfaces of the circuit board. And also, the plurality of memories enable an one-side transmission image of a next circuit board to be ready and stored during extracting an other-side transmission image of the present circuit board.

A both-side transmission image of the circuit board finished being mounted on its both side surfaces is obtained by the image reader 17 in the second inspection section 3. And the both-side transmission image is adjusted by the third response adjustment devices 18 so as to gain characteristic of the both-side transmission image is made into uniform in the referred spatial frequency range. The adjusted both-side transmission image is input into both the subtracter 20 and the second standard mark calculator 19.

The one-side transmission image of the circuit board is taken out from either second or third memory 12 or 13 selected by the second switching device 14 and further adjusted by the second response adjustor 15 as above while the both-side transmission image of the circuit board is obtained as above. The adjusted one-side transmission image is input into both the subtracter 20 and the first standard mark calculator 16.

In the first and second standard mark calculators 16 and 19, position information concerning standard marks are read from the one-side transmission image and the both-side transmission image respectively. And, gap amounts between information concerning reference points on the circuit board which have given in advance and the above information concerning the standard marks are calculated respectively there. And then, the gap amounts are input from the first and second standard mark calculators 16, 19, into the subtracter 20 respectively.

In the subtracter 20, an amendment calculation is performed in order to amend a slight gap under one picture element pitch between the foregoing transmission images by using the above gap amounts, and the adjusted one-side transmission image and the adjusted both-side transmission image are aligned.

And then, an other-side transmission image is obtained by subtracting the adjusted one-side transmission image from the adjusted both-side transmission image. A soldering inspection of the other-side surface is performed by the second judgment device 21 applying the above other-side transmission image.

The above mentioned alignment enables gap amount between one-side transmission image and both-side transmission image to be under one picture element pitch when the other-side transmission image is obtained by subtracting the adjusted one-side transmission image from the adjusted both-side transmission image. The X-rays transmission image is made as analog signal detected by X-rays detector and so on, and further is discreted every referred times by an A/D converter. This referred time corresponds to one picture element pitch of an image. Accordingly, if the subtraction for obtaining the other-side transmission image is performed without the alignment of which error is under one picture element pitch, an obtained image will have an error over one picture element pitch.

This is one of factors which cause a mistake on the judgement of the soldering-inspection. Therefore, in this embodiment of the present invention, the above factor of causing the mistake on the judgement is eliminated by means of a two-dimensional amendment concerning a shade level (X-rays transmission quantity level) of one picture element at a required position.

For example, there is a two-dimensional matrix $Ya[j,k]$ which shows a shade level of an image. Hereon, j is a natural number which can change in a range from 1 to m, and k is a natural number which can change in a range from 1 to n. Further, there are a Vector x1a having m number of elements and a Vector y1a having n number of elements. A value of a shade level can be shown by the matrix and vectors as follows.

$$Ya[j,k]=y(x1a[j], x2a[k]) \qquad (1)$$

Hereon, Ya is a value of the shade level discreted within one plane. y is an analog value of the shade level.

Figure 5:
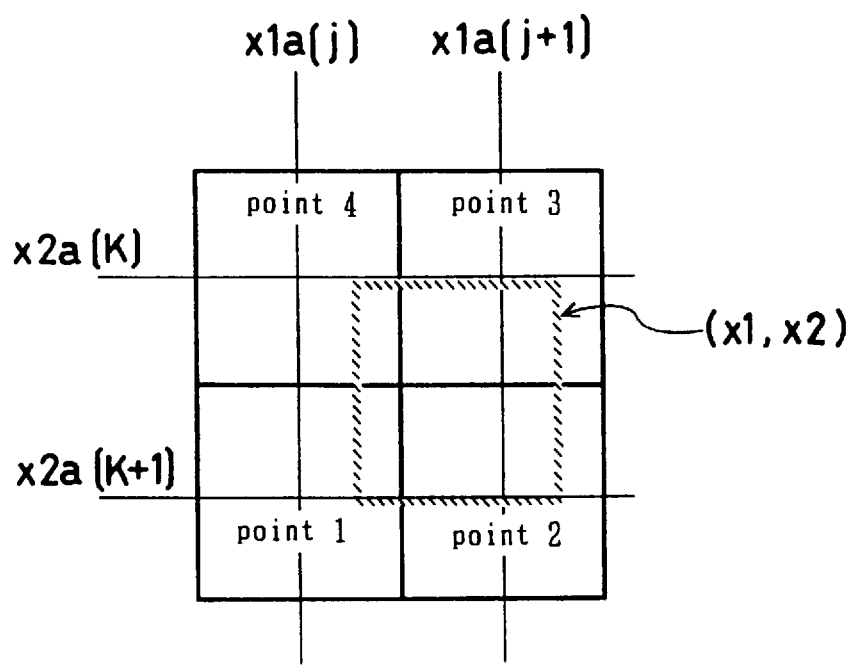
FIG. 5 is a model figure for explaining a condition of alignment which aligns an one-side transmission image and an both-side transmission image with amending a scant gap under picture element pitch.

An analog value of the shade level y which we would like reason by analogy by means of the amendment is a value on a spot (x1, x2) which is not included in points (x1a[j], x2a[k]). Now, we will think about 4 points which surrounds the spot (x1, x2) as shown in FIG. 5. Square surrounding each point in FIG. 5 shows an element. j and k are defined as follows.

$$x1a[j] \leq x1 \leq x1a[j+1] \qquad (2)$$

$$x2a[k] \leq x2 \leq x2a[k+1] \qquad (3)$$

A shade level on each point is defined as follows.

$$y1=Ya[j,k] \qquad (4)$$

$$y2=Ya[j+1,k] \qquad (5)$$

$$y3=Ya[j+1,k+1] \qquad (6)$$

$$y4=Ya[j,k+1] \qquad (7)$$

The simplest two-dimensional amendment is performed as follows.

$$t=(x1-x1a[j])/(x1a[j+1]-x1a[j]) \qquad (8)$$

$$u=(x2-x2a[k])/(x2a[k+1]-x2a[k]) \qquad (9)$$

Accordingly, the shade level on the spot (x1,x2) is as follows.

$$y=(x1,x2)=(1-t)(1-u)y1+t(1-u)y2+tuy3+(1-t)uy4 \qquad (10)$$

The foregoing expression (10) implies putting a weight to a shade level on the required position in accordance with an area ratio of a plurality of picture elements occupied by the spot (x1,x2) and summing them.

Furthermore, in case of making an improved accuracy on the amendment, it is preferable that mx n blocks including the spot (x1,x2) are selected, an one-dimensional amendment is performed with m number of the picture elements in a direction of x2 and an one-dimensional amendment is performed with n number of the picture elements in a direction of x1. A polynomial such as a formula of Lagrange and so on, a rational function and a spline function can be used in one dimension amendment.

The one-side transmission image and the both-side transmission image to be input into the subtracter 20 are the transmission images of which responses have been adjusted as already described. The above-mentioned adjustment of response is performed as follows.

The analog signal concerning a X-rays transmission image detected by the X-ray detector is converted into digital data. Components of spatial frequency are extracted from these digital images. The components of spatial frequency are multiplied by an adjustment factors for making response characteristic nearly uniform within a referred spatial frequency range fixed in advance.

And then, the transmission image is adjusted by inverse transforming multiplication results so as to make the response characteristic into uniform within the referred spatial frequency range. The above-mentioned adjustment factor is obtained as follows. Digital images are collected from various kind of objects which have natural spatial frequencies respectively. The adjustment factors are fixed so as to make a response into uniform through all spatial frequencies of the collected images. The above-mentioned referred spatial frequency range implies, for example, a range to which both spatial frequencies of the one-side transmission image and the both-side transmission image belong.

An other-side transmission image having fine accuracy can be obtained by means of extracting a subtracted image applying the above mentioned adjusted one-side transmission image and both-side transmission image of which response characteristics are adjusted so as to be nearly uniformed in the referred spatial frequency range as above mention.

The concrete example which extracts the subtracted image (i.e. the other-side transmission image) applying the above mentioned adjusted one-side transmission image and both-side transmission image will be shown below.

Figure 6:
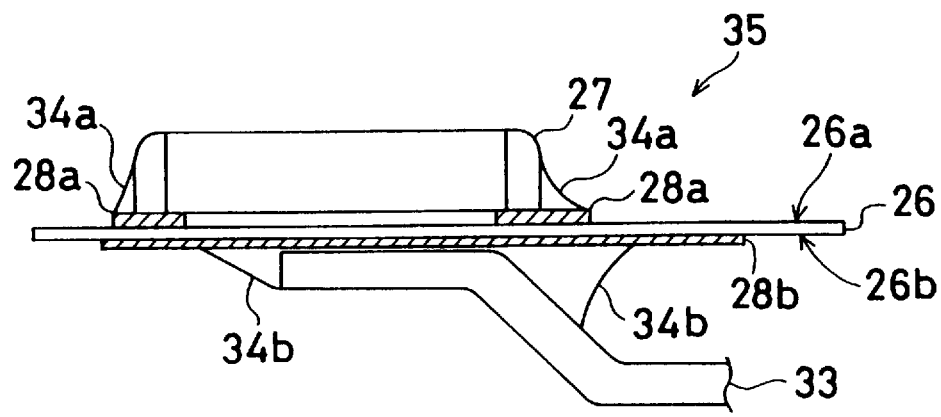
FIG. 6(a) shows an example of a both-side surfaces mounted circuit board.
FIG. 6(b) shows an example of a X-rays transmission amount distribution concerning a both-side surfaces mounted circuit board.
Figure 6:
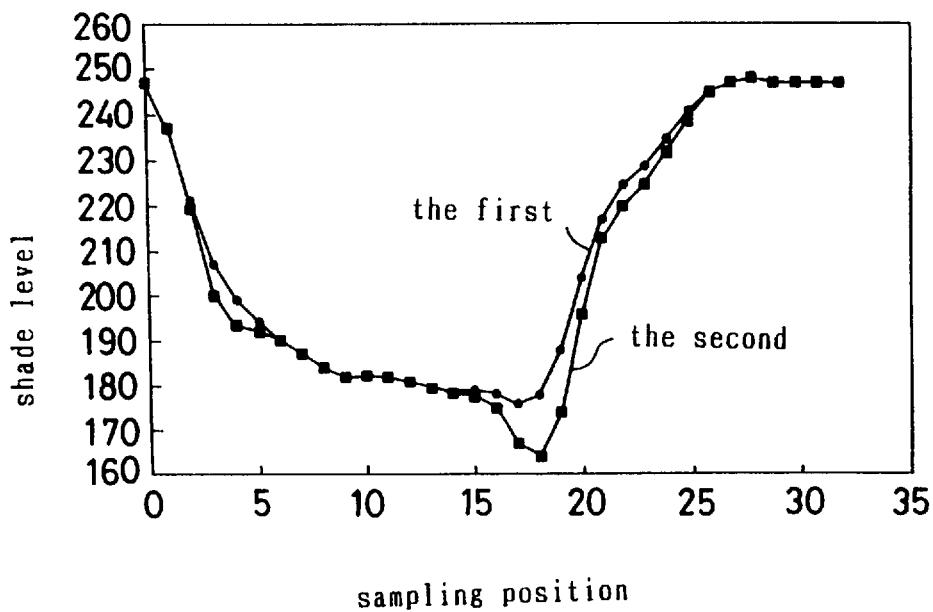
Figure 7:
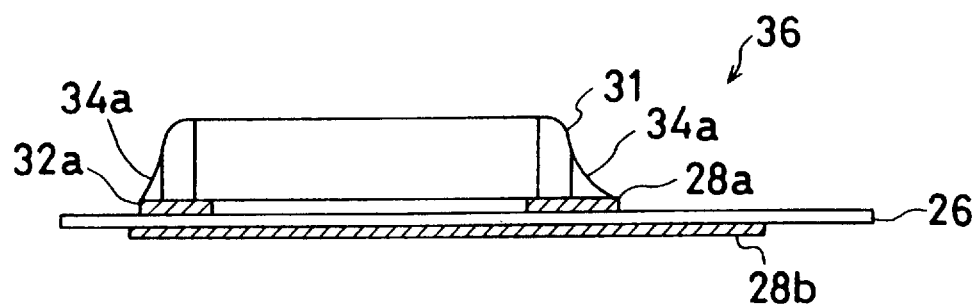
FIG. 7(a) shows an example of an one-side surface mounted circuit board.
FIG. 7(b) shows an example of a X-rays transmission amount distribution concerning an one-side surface mounted circuit board.
Figure 7:
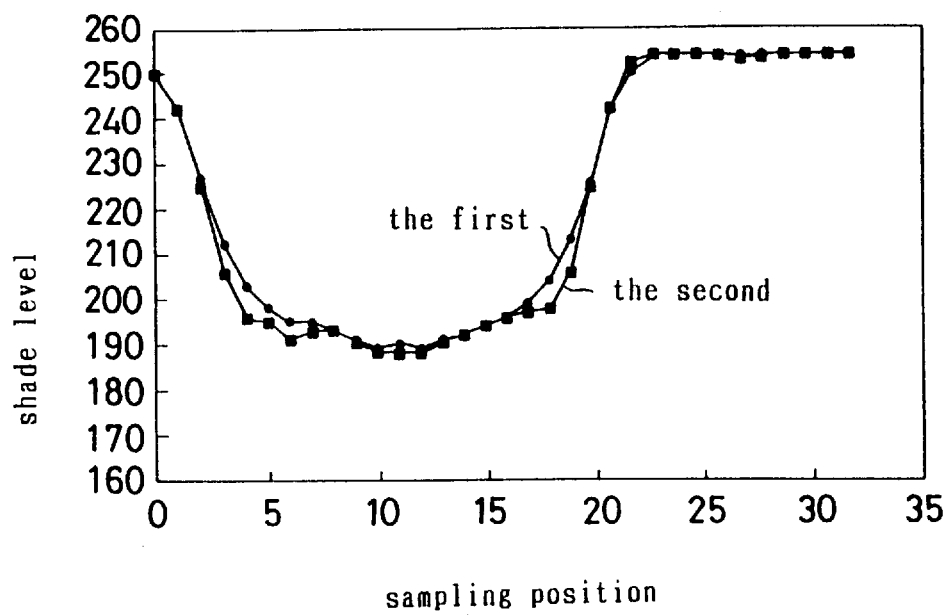

A chip component 27 is fixed by soldering at solder lands 28a formed on an one-side surface 26a of a circuit board 35 as shown in FIG. 6(a). A lead 33 of another component is fixed by soldering on an other-side surface 26b of the circuit board 35 as shown in FIG. 6(a). Their transmission images could overlap each other. A shade level is shown in FIG. 6(b), which shows X-rays transmission amount distributions concerning the above mentioned circuit board 35 of which both side surfaces are mounted with components. The circuit board 35 is shown in FIG. 7(a), of which one side surface is only mounted with components before the above mentioned circuit board 35 of which both side surfaces are mounted with components. A shade level is shown in FIG. 7(b), which shows X-rays transmission amount distributions concerning the circuit board 35 shown in FIG. 7(a). A shade level is shown in FIG. 8(b), which shows differences between the above mentioned X-rays transmission amount distributions shown in FIG. 6(b) and FIG. 7(b).

Figure 8:
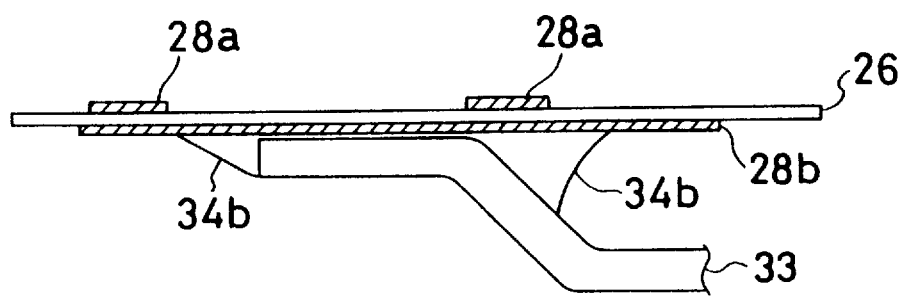
FIG. 8(a) shows an example of an other-side surface mounted circuit board.
FIG. 8(b) shows an example of a X-rays transmission amount distributions concerning an other-side surface mounted circuit board as a model and a subtracted transmission image which is obtained by subtracting the one-side transmission image from the both-side transmission image.
Figure 8:
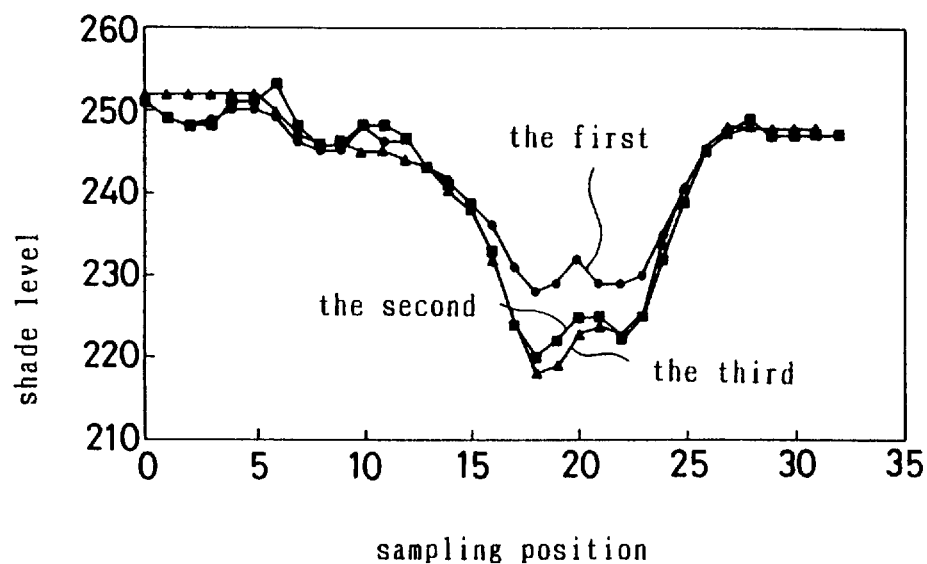
Figure 9:
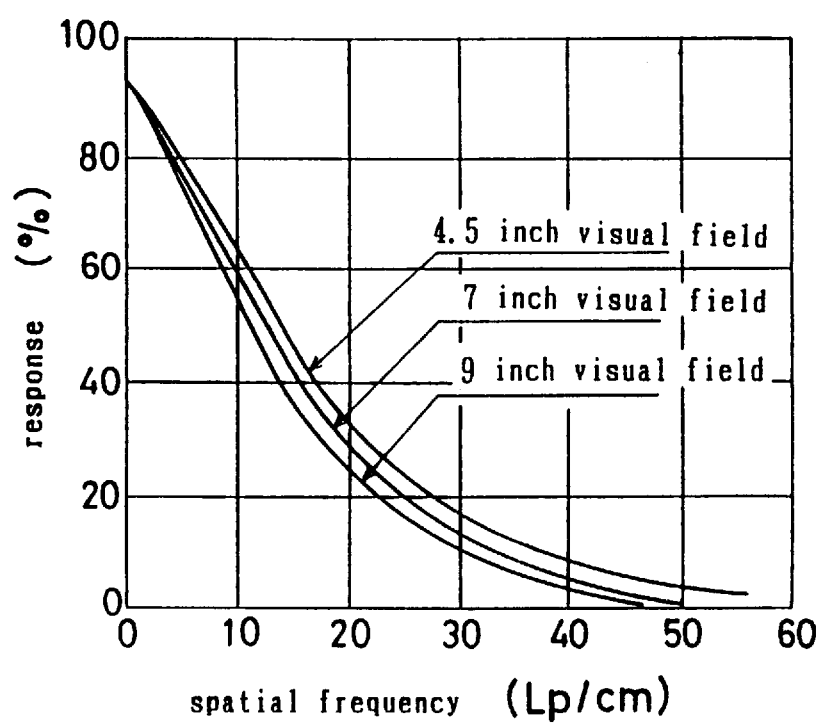
FIG. 9 shows one of examples concerning a response characteristics of X-rays detector.

There are two kind of X-rays transmission amount distributions shown in FIG. 6(b), FIG. 7(b) and FIG. 8(b) respectively. The first X-rays transmission amount distribution is the distribution in the case of non-applying adjustment concerning response of transmission image. The second X-rays transmission amount distribution is the distribution in the case of applying adjustment concerning response of transmission image.

Further, the third X-rays transmission amount distribution is added in FIG. 8(b). The third X-rays transmission amount distribution is the distribution concerning another circuit board as a comparative example for supposing the above mentioned circuit board 35 of which other side surface is only mounted with components, and which is the distribution in the case of applying adjustment concerning response of transmission image.

The transmission image concerning the above mentioned circuit board 35 of which other side surface is only mounted with components can not obtained indeed. Therefore, the third X-rays transmission amount distribution is offered as a ideal model in order to verify how much the subtracted image applying the response adjustment closes to the other-side transmission image concerning the circuit board 35 of which other side surface is only mounted with components. It can be found that the subtracted image after adjusting responses shown in FIG. 8(b) approximates to the transmission image concerning the ideal model mounted on only other side surface.

According to these examples, the average is 3.8% and the maximum is 12.1% concerning the difference between the subtracted image without adjusting responses and the transmission image of the ideal model. In case of adjusting responses, the average reduces into 1.2% and the maximum reduces into 4.0%. By adjusting responses as above mention, the other-side transmission image can be extracted with high accuracy from the both-side transmission image. And the effect in which the soldering inspection becomes accurate will be obtained as a result. Moreover, the one-side transmission image and the both-side transmission image can be inspected with same inspection standards since response characteristics of both images are identified.

This invention as above mentioned has the following effects.

Even though the one-side transmission image and the both-side transmission image have different spatial frequencies respectively, the other-side transmission image having fine accuracy can be extracted by means of the adjustment which makes response characteristics concerning spatial frequency into uniform in the referred spatial frequency range. As a result, the inspection accuracy can be improved.

Moreover, the other-side transmission image having finer accuracy can be extracted by means of alignment applying amendment of amending the gap between the one-side transmission image and the both-side transmission image to calculate the gap amount under one picture element pitch when the subtracted image is made by subtracting the one-side transmission image from the both-side transmission image.

And the transfer speed is improved by means of proper transferring of the-compressed and coded one-side transmission image to necessary processes for extracting the other-side transmission image.

And also, the present invention has a construction as follows. The transferred one-side transmission image is memorized by the plurality of image memories in order of the transformation and taken out properly from them in accordance with processes for extracting the other-side transmission image in order to be subtracted from the both-side transmission image.

Because of the above construction, this invention has the further following effects.

The one-side transmission image and the other-side transmission image can undergo soldering inspections at the same time. Also, the surface mounted circuit board can undergo soldering inspection in accordance with a flow of manufacturing processes of the surface mounted circuit board since an one-side transmission image of a next circuit board can be ready during the inspection of the present circuit board.

INDUSTRIAL APPLICABILITY

The present invention is suitable for a method and an apparatus for soldering inspection of a surface mounted circuit board, which improves an inspection accuracy by means of obtaining a highly accurate X-rays transmission image corresponding to a real shape of the mounted surface.

We claim:

1. An apparatus for inspecting soldering conditions from a transmission image applying radiating X-rays, comprising
   a response adjustment means wherein a response of said transmission image is adjusted so as to make its response characteristic into uniform in a referred spatial frequency range on the basis of a response characteristic to a spatial frequency concerning an image radiographic system and an image processing system at the time of reading the transmission image and a soldering inspection means for inspecting soldering conditions using said transmission image of which response is adjusted.

2. An apparatus for soldering inspection of a surface mounted circuit board, comprising an one-side transmission image reading means for obtaining an one-side transmission image to radiate X-rays to a circuit board of which only one side surface is mounted with components, a both-side transmission image reading means for obtaining a both-side transmission image to radiate X-rays to said circuit board of which both side surfaces are mounted with components, a subtraction means for subtracting said one-side transmission image from said both-side transmission image in order to obtain an other-side transmission image and an other-side soldering inspection means for inspecting soldering conditions using said other-side transmission image, wherein said subtraction means includes an alignment means wherein information concerning standard marks are read from said one-side transmission image and said both-side transmission image respectively, gap amounts between information concerning reference points on said circuit board which have given in advance and said information concerning said standard marks are calculated respectively, a gap between said one-side transmission image and said both-side transmission image is calculated using said gap amounts, which is under one picture element pitch and both one-side transmission image and said both-side transmission image are aligned.

3. A method for soldering inspection of a surface mounted circuit board, including an one-side transmission image reading process for obtaining an one-side transmission image to radiate X-rays to a circuit board of which only one side surface is mounted with components, a both-side transmission image reading process for obtaining a both-side transmission image to radiate X-rays to said circuit board of which both side surfaces are mounted with components, a subtraction process for subtracting said one-side transmission image from said both-side transmission image in order to obtain an other-side transmission image and an other-side soldering inspection process for inspecting soldering conditions using said other-side transmission image, wherein said subtraction process includes an alignment process wherein information concerning standard marks are read from said one-side transmission image and said both-side transmission image respectively, gap amounts between information concerning reference points on said circuit board which have been given in advance and said information concerning said standard marks are calculated respectively, a gap between said one-side transmission image and said both-side transmission image is calculated using said gap amounts, which is under one picture element pitch and both said one-side transmission image and said both-side transmission image are aligned.

4. A method for inspecting soldering conditions from a transmission image applying radiating X-rays, including a response adjustment process wherein a response of said transmission image is adjusted so as to make its response characteristic into uniform in a referred spatial frequency range on the basis of a response characteristic to a spatial frequency concerning an image radiographic system and an image processing system at the time of reading the transmission image and a soldering inspection process for inspecting soldering conditions using said transmission image of which response is adjusted.

5. An apparatus for soldering inspection of a surface mounted circuit board, comprising an one-side transmission image reading means for obtaining an one-side transmission image to radiate X-rays toward a circuit board of which only one side surface is mounted with components, an one-side soldering-inspection means for inspecting soldering conditions using said one-side transmission image, a both-side transmission image reading means for obtaining a both-side transmission image to radiate X-rays to said circuit board of which both side surfaces are mounted with components, a response adjustment means for adjusting responses of said one-side transmission image and both-side transmission image so as to make their response characteristics into uniform in a referred spatial frequency range on the basis of response characteristics to a spatial frequency concerning an image radiographic system and an image processing system in said reading means, a subtraction means for subtracting said one-side transmission image of which response adjusted from said both-side transmission image of which response adjusted in order to obtain an other-side transmission image, and an other-side soldering inspection means for inspecting soldering conditions using said other-side transmission image.

6. An apparatus for soldering inspection of a surface mounted circuit board according to claim 5, wherein said one-side transmission image and said both-side transmission image is adjusted by said response adjustment means so as to make gain characteristics of them into uniform in said referred spatial frequency range.

7. An apparatus for soldering inspection of a surface mounted circuit board according to claim 5, wherein said subtraction means for subtracting said one-side transmission image from said both-side transmission image includes an alignment means wherein information concerning standard marks are read from said one-side transmission image and said both-side transmission image respectively, gap amounts between information concerning reference points on said circuit board which have given in advance and said information concerning said standard marks are calculated respectively, a gap between said one-side transmission image and said both-side transmission image is calculated using said gap amounts, which is under one picture element pitch and both one-side transmission image and said both-side transmission image are aligned.

8. An apparatus for soldering inspection of a surface mounted circuit board according to claim 5, further including one means wherein said one-side transmission image is compressed, coded and transferred properly toward necessary means for obtaining said other-side transmission image.

9. An apparatus for soldering inspection of a surface mounted circuit board according to claim 8, further including another means wherein said compressed and coded one-side transmission image is decoded, expanded and memorized.

10. A method for soldering inspection of a surface mounted circuit board, including an one-side transmission image reading process for obtaining an one-side transmission image to radiate X-rays to a circuit board of which only one side surface is mounted with components, an one-side soldering inspection process for inspecting soldering conditions using said one-side transmission image, a both-side transmission image reading process for obtaining a both-side transmission image to radiate X-rays to said circuit board of which both side surfaces are mounted with components, a response adjustment process for adjusting responses of said one-side transmission image and both-side transmission image so as to make their response characteristics into uniform in a referred spatial frequency range on the basis of response characteristics to a spatial frequency concerning an image radiographic system and an image processing system at said reading processes, a subtraction process for subtracting said one-side transmission image of which response adjusted from said both-side transmission image of which response adjusted in order to obtain an other-side transmission image, and an other-side soldering inspection process for inspecting soldering conditions using said other-side transmission image.

11. A method for soldering inspection of a surface mounted circuit board according to claim 10, wherein said one-side transmission image and said both-side transmission image is adjusted so as to make gain characteristics of them into uniform in said referred spatial frequency range at said response adjustment process.

12. A method for soldering inspection of a surface mounted circuit board according to claim 10, wherein said subtraction process for subtracting said one-side transmission image from said both-side transmission image includes an alignment process wherein information concerning standard marks are read from said one-side transmission image and said both-side transmission image respectively, gap amounts between information concerning reference points on said circuit board which have given in advance and said information concerning said standard marks are calculated respectively, a gap between said one-side transmission image and said both-side transmission image is calculated using said gap amounts, which is under one picture element pitch and both one-side transmission image and said both-side transmission image are aligned.

13. A method for soldering inspection of a surface mounted circuit board according to claim 10, further including one process wherein said one-side transmission image is compressed, coded and transferred properly toward necessary processes for obtaining said other-side transmission image.

14. A method for soldering inspection of a surface mounted circuit board according to claim 13, further including another process wherein said compressed and coded one-side transmission image is decoded, expanded and memorized.

15. An image reader comprising a recording means for recording a radiation transmission image of a flat circuit board onto a recording plate which consists of a radiate-out phosphor material, wherein said radiation transmission image is obtained by means of radiating a radiation perpendicularly from a radiation source positioned above said circuit board towards said recording plate below said circuit board, a reading means for reading said recorded image on said recording plate, wherein a reading operation is performed by catching a radiate-out luminous light which is irradiated out from said recording plate by means of irradiating an excitation light onto said recording plate, an erasing means for erasing said recorded image on said recording plate, wherein an erasing operation is performed by exposing said recording plate to light, a circulation conveyance means for conveying said recording plate circularly within a first horizontal plane, wherein said recording plate is conveyed circularly in order of said recording means, said reading means, said erasing means and said recording means again, and a circuit board conveyance means for conveying said circuit board within a second horizontal plane which is located upward in parallel with said first horizontal plane.

16. An image reader according to claim 15, wherein said recording plate is conveyed within said first horizontal plane circularly while sucked by a vacuum suction device.

17. An image reader according to claim 15, wherein said reading means has a lifting device for adjusting a distance between said circuit board and said recording plate.

18. An image reader according to claim 15, wherein said reading means has a plurality of scanning devices along said conveying direction and the scanning devices irradiate excitation lights on one recording plate.

19. An image reader according to claim 18, wherein said plurality of scanning devices share light beams from a common light source with each other.

20. An image reader according to claim 18, wherein said plurality of scanning devices irradiate light beams of which irradiation intensities are uniform.

* * * * *